(12) United States Patent
Koele et al.

(10) Patent No.: US 7,812,214 B2
(45) Date of Patent: Oct. 12, 2010

(54) ABSORBENT ARTICLE FEATURING A LAMINATED MATERIAL WITH A LOW POISSON'S RATIO

(75) Inventors: Matthew L. Koele, Random Lake, WI (US); Elizabeth D. Gadsby, Marietta, GA (US); Thomas M. Flicker, Neenah, WI (US); Jason S. Fairbanks, Gainesville, GA (US); Courtney Shea, Winston Salem, NC (US); Ann L. McCormack, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 491 days.

(21) Appl. No.: 11/365,543

(22) Filed: Feb. 28, 2006

(65) Prior Publication Data
US 2007/0203467 A1  Aug. 30, 2007

(51) Int. Cl.
*A61F 13/15* (2006.01)
*A61F 13/20* (2006.01)

(52) U.S. Cl. .................................. 604/367; 604/385.01
(58) Field of Classification Search ............ 604/385.01, 604/367–374
See application file for complete search history.

(56) References Cited

U.S. PATENT DOCUMENTS

| | | | |
|---|---|---|---|
| 3,849,241 A | 11/1974 | Butin et al. |
| 4,663,220 A | 5/1987 | Wisneski et al. |
| 4,704,116 A | 11/1987 | Enloe |
| 4,725,473 A | 2/1988 | Van Gompel et al. |
| 4,825,473 A | 5/1989 | Brame |
| 4,940,464 A | 7/1990 | Van Gompel et al. |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,213,881 A | 5/1993 | Timmons et al. |
| 5,224,405 A | 7/1993 | Pohjola |
| 5,226,992 A | 7/1993 | Morman |
| 5,486,166 A | 1/1996 | Bishop et al. |
| 5,490,846 A | 2/1996 | Ellis et al. |
| 5,612,118 A | 3/1997 | Schleinz et al. |

(Continued)

FOREIGN PATENT DOCUMENTS

EP  0 217 032 A2  4/1987

(Continued)

OTHER PUBLICATIONS

American Society for Testing Materials (ASTM) Designation: E 132-04, "Standard Test Method for Poisson's Ratio at Room Temperature," published Apr. 2004, pp. 1-3.

*Primary Examiner*—Michele Kidwell
(74) *Attorney, Agent, or Firm*—Randall W. Fieldhack

(57) ABSTRACT

Disclosed is an absorbent article defining a longitudinal direction and a lateral direction perpendicular to the longitudinal direction, the absorbent article including an outercover, the outercover comprising a laminated material including two layers; an absorbent body disposed adjacent the outercover; and a graphic associated with the outercover, wherein the laminated material exhibits a Poisson's Ratio less than 1.0 at 4 percent longitudinal strain using ASTM-E132. The laminated material optimally exhibits a Poisson's Ratio less than 0.75 at 4 percent longitudinal strain using ASTM-E132. The laminated material more optimally exhibits a Poisson's Ratio less than 0.4 at 4 percent longitudinal strain using ASTM-E132.

21 Claims, 4 Drawing Sheets

U.S. PATENT DOCUMENTS

| | | | |
|---|---|---|---|
| 5,620,431 A * | 4/1997 | LeMahieu et al. | 604/385.25 |
| 5,645,542 A | 7/1997 | Anjur et al. | |
| 5,766,389 A | 6/1998 | Brandon et al. | |
| 5,837,352 A | 11/1998 | English et al. | |
| 5,843,057 A | 12/1998 | McCormack | |
| 5,883,028 A | 3/1999 | Morman et al. | |
| 5,964,743 A | 10/1999 | Abuto et al. | |
| 6,096,014 A | 8/2000 | Haffner et al. | |
| 6,156,421 A | 12/2000 | Stopper et al. | |
| 6,231,557 B1 | 5/2001 | Krautkramer et al. | |
| 6,231,715 B1 | 5/2001 | Schleinz et al. | |
| 6,297,424 B1 * | 10/2001 | Olson et al. | 604/361 |
| 6,362,389 B1 | 3/2002 | McDowall et al. | |
| 6,552,245 B1 | 4/2003 | Roessler et al. | |
| 6,645,190 B1 | 11/2003 | Olson et al. | |
| 2004/0030431 A1 | 2/2004 | Popp et al. | |
| 2005/0042962 A1 | 2/2005 | McCormack et al. | |
| 2005/0142331 A1 * | 6/2005 | Anderson et al. | 428/152 |

FOREIGN PATENT DOCUMENTS

| | | |
|---|---|---|
| WO | WO 00/37009 A2 | 6/2000 |
| WO | WO 01/88245 A2 | 11/2001 |
| WO | WO 03/051254 A2 | 6/2003 |

* cited by examiner

ABSORBENT ARTICLE FEATURING A LAMINATED MATERIAL WITH A LOW POISSON'S RATIO

BACKGROUND OF THE INVENTION

The present invention relates to absorbent articles that include an outercover and other structures. More specifically, the invention relates to an absorbent article such as training pants that incorporate a laminated material in its outercover or other structure, where the laminated material exhibits a low Poisson's Ratio.

Absorbent articles, such as children's training pants, have been designed with an outercover or other structure employing a material in which a nonwoven is laminated to a printed film. Unfortunately, in certain circumstances, such outercovers or other structures may not be completely satisfactory. For example, the printing on the outercover or other structure may appear dull or faded because the printed film is overlaid with a nonwoven layer. Moreover, attempts to print the outercover or other structure subsequent to lamination compromise the ability to register the graphics on such laminated materials because the laminated materials do not stretch as easily as a single layer of film. This leads to the application of much higher tension force levels to register the graphics, resulting in such materials necking down in the cross-machine or transverse direction to widths that are too narrow for acceptable processing. Narrow web widths can result in exposed adhesive beads intended to connect the laminated material with the rest of the article. This exposed adhesive bead usually yields a non-functional and/or non-acceptable absorbent article.

Thus, there is a need for an absorbent article with a laminated material exhibiting a low Poisson's Ratio to limit the necking in the laminated material.

SUMMARY OF THE INVENTION

In one aspect, the present invention is directed to an absorbent article defining a longitudinal direction and a lateral direction perpendicular to the longitudinal direction, the absorbent article including an outercover, the outercover comprising a laminated material including two layers; an absorbent body disposed adjacent the outercover; and a graphic associated with the outercover, wherein the laminated material exhibits a Poisson's Ratio less than 1.0 at 4 percent longitudinal strain using ASTM-E132. The laminated material optimally exhibits a Poisson's Ratio less than 0.75 at 4 percent longitudinal strain using ASTM-E132. The laminated material more optimally exhibits a Poisson's Ratio less than 0.4 at 4 percent longitudinal strain using ASTM-E132.

In another aspect, the present invention is directed to an absorbent article defining a longitudinal direction and a lateral direction perpendicular to the longitudinal direction, the absorbent article including an outercover, the outercover comprising a laminated material including two layers; an absorbent body disposed adjacent the outercover; and a graphic associated with the outercover, wherein the laminated material exhibits a Poisson's Ratio less than 2.0 at 6 percent longitudinal strain using ASTM-E132. The laminated material optimally exhibits a Poisson's Ratio less than 1.5 at 6 percent longitudinal strain using ASTM-E132. The laminated material more optimally exhibits a Poisson's Ratio less than 0.5 at 6 percent longitudinal strain using ASTM-E132.

In yet another aspect, the present invention is directed to an absorbent article defining a longitudinal direction and a lateral direction perpendicular to the longitudinal direction, the absorbent article including a laminated material including two layers; a graphic associated with the laminated material; and an absorbent body disposed in the absorbent article, wherein the graphic is registered to the absorbent body, and wherein the laminated material exhibits a Poisson's Ratio less than 1.0 at 4 percent longitudinal strain using ASTM-E132.

In still another aspect, the present invention is directed to a laminated material for use in a product, the laminated material including a film layer including a film; and a nonwoven layer including a spunbond nonwoven, wherein the laminated material exhibits a Poisson's Ratio less than 1.0 at 4 percent longitudinal strain using ASTM-E132.

The above-mentioned and other aspects of the present invention will become more apparent, and the invention itself will be better understood by reference to the drawings and the following description of the drawings.

BRIEF DESCRIPTION OF THE DRAWINGS

Corresponding reference characters indicate corresponding parts throughout the drawings.

DEFINITIONS

Figure 1:
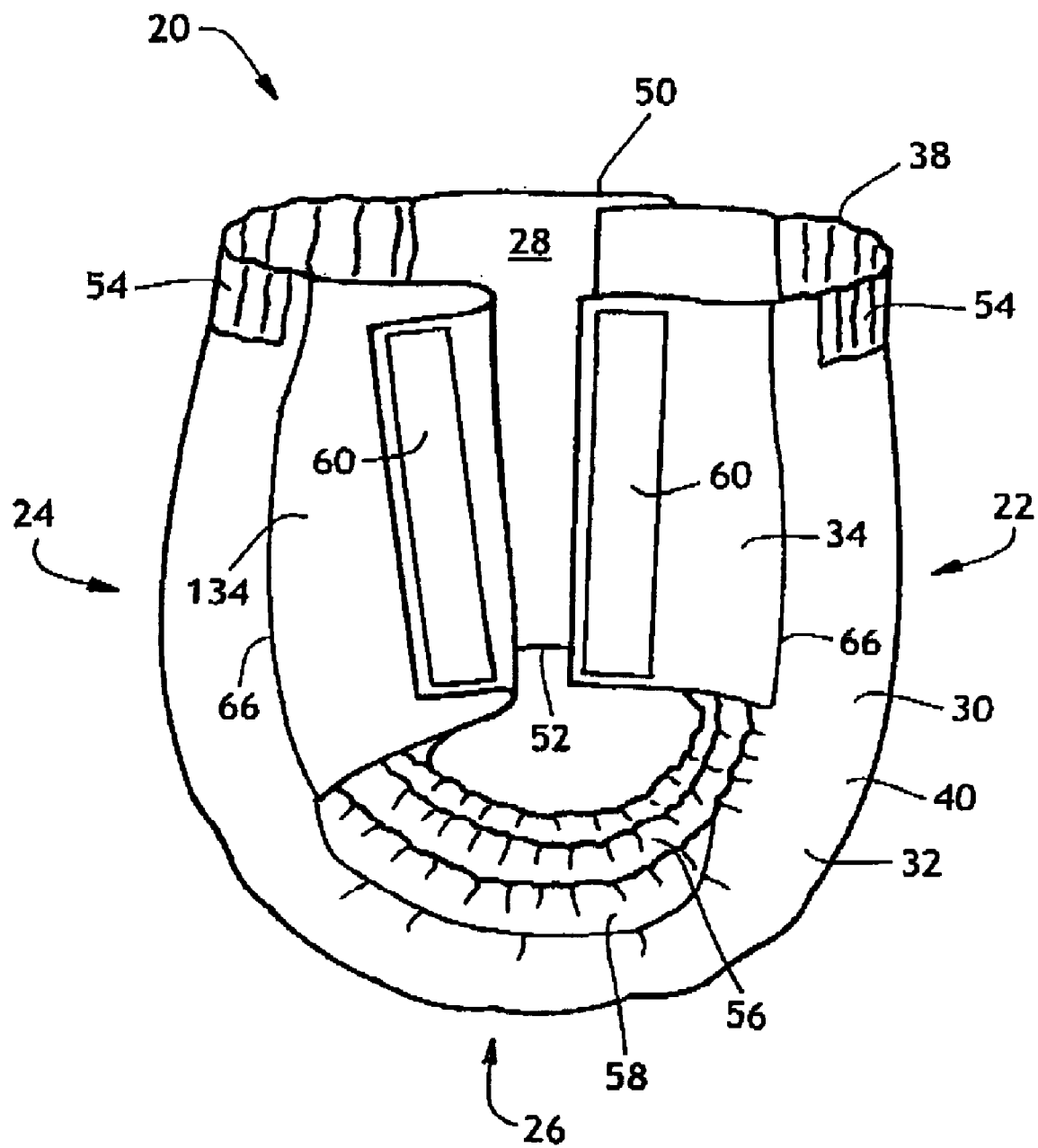
FIG. 1 representatively illustrates a side view of a pair of training pants with a mechanical fastening system of the pants shown fastened on one side of the training pants and unfastened on the other side of the training pants.

Within the context of this specification, each term or phrase below includes the following meaning or meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers are collected on a forming surface, such as provided by a foraminous belt. The forming surface may include a gas-pervious material that has been placed onto the forming surface.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Disposable" refers to articles which are designed to be discarded after a limited use rather than being laundered or otherwise restored for reuse.

The terms "disposed on," "disposed along," "disposed with," or "disposed toward" and variations thereof are intended to mean that one element can be integral with another element, or that one element can be a separate structure bonded to or placed with or placed near another element.

"Elastic," "elasticized," "elasticity," and "elastomeric" mean that property of a material or composite by virtue of which it tends to recover its original size and shape after removal of a force causing a deformation. Suitably, an elastic material or composite can be elongated by at least 25 percent (to 125 percent) of its relaxed length and will recover, upon release of the applied force, at least 40 percent of its elongation.

"Extensible" refers to a material or composite which is capable of extension or deformation without breaking, but does not substantially recover its original size and shape after removal of a force causing the extension or deformation. Suitably, an extensible material or composite can be elongated by at least 25 percent (to 125 percent) of its relaxed length.

"Fiber" refers to a continuous or discontinuous member having a high ratio of length to diameter or width. Thus, a fiber may be a filament, a thread, a strand, a yarn, or any other member or combination of these members.

"Hydrophilic" describes fibers or the surfaces of fibers which are wetted by aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 degrees are designated "wettable" or hydrophilic, and fibers having contact angles greater than 90 degrees are designated "nonwettable" or hydrophobic.

"Layer" when used in the singular can have the dual meaning of a single element or a plurality of elements.

"Liquid impermeable," when used in describing a layer or multi-layer laminate means that liquid, such as urine, will not pass through the layer or laminate, under ordinary use conditions, in a direction generally perpendicular to the plane of the layer or laminate at the point of liquid contact.

"Liquid permeable" refers to any material that is not liquid impermeable.

"Meltblown" refers to fibers formed by extruding a molten thermoplastic material through a plurality of fine, usually circular, die capillaries as molten threads or filaments into converging high velocity gas (e.g., air) streams, generally heated, which attenuate the filaments of molten thermoplastic material to reduce their diameters. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241, issued on Nov. 19, 1974 to Butin et al. Meltblowing processes can be used to make fibers of various dimensions, including macrofibers (with average diameters from about 40 to about 100 microns), textile-type fibers (with average diameters between about 10 and 40 microns), and microfibers (with average diameters less than about 10 microns). Meltblowing processes are particularly suited to making microfibers, including ultra-fine microfibers (with an average diameter of about 3 microns or less). A description of an exemplary process of making ultra-fine microfibers may be found in, for example, U.S. Pat. No. 5,213,881, issued on May 25, 1993 to Timmons et al. Meltblown fibers may be continuous or discontinuous and are generally self bonding when deposited onto a collecting surface.

"Member" when used in the singular can have the dual meaning of a single element or a plurality of elements.

"Nonwoven" and "nonwoven web" refer to materials and webs of material that are formed without the aid of a textile weaving or knitting process. For example, nonwoven materials, fabrics or webs have been formed from many processes such as, for example, meltblowing processes, spunbonding processes, air laying processes, and bonded carded web processes.

"Stretchable" means that a material can be stretched, without breaking, by at least 25 percent (to 125 percent of its initial (unstretched) length) in at least one direction. Elastic materials and extensible materials are each stretchable materials.

"Superabsorbent material" refers to a water-swellable, water-insoluble organic or inorganic material capable, under the most favorable conditions, of absorbing at least about ten times its weight and, more desirably, at least about thirty times its weight in an aqueous solution containing about 0.9 weight percent sodium chloride.

These terms may be defined with additional language in the remaining portions of the specification.

DETAILED DESCRIPTION

Referring now to the drawings and in particular to FIG. 1, an exemplary absorbent article of the present invention is representatively illustrated in the form of children's toilet training pants and is indicated in its entirety by the reference numeral 20. The pants 20 may or may not be disposable, which refers to articles that are intended to be discarded after a limited period of use instead of being laundered or otherwise conditioned for reuse. It should also be understood that the present invention is suitable for use with various other absorbent articles intended for personal wear, including but not limited to diapers, feminine hygiene products, incontinence products, medical garments, surgical pads and bandages, other personal care or health care garments, and the like without departing from the scope of the present invention.

By way of illustration only, various materials and methods for constructing training pants such as the pants 20 of the various aspects of the present invention are disclosed in PCT Patent Application WO 00/37009, published on Jun. 29, 2000 by A. Fletcher et al.; U.S. Pat. No. 4,940,464, issued on Jul. 10, 1990 to Van Gompel et al.; U.S. Pat. No. 5,766,389, issued on Jun. 16, 1998 to Brandon et al.; and U.S. Pat. No. 6,645,190, issued on Nov. 11, 2003 to Olson et al.; which are incorporated herein by reference to the extent that they are consistent (i.e., not in conflict) herewith.

Figure 2:
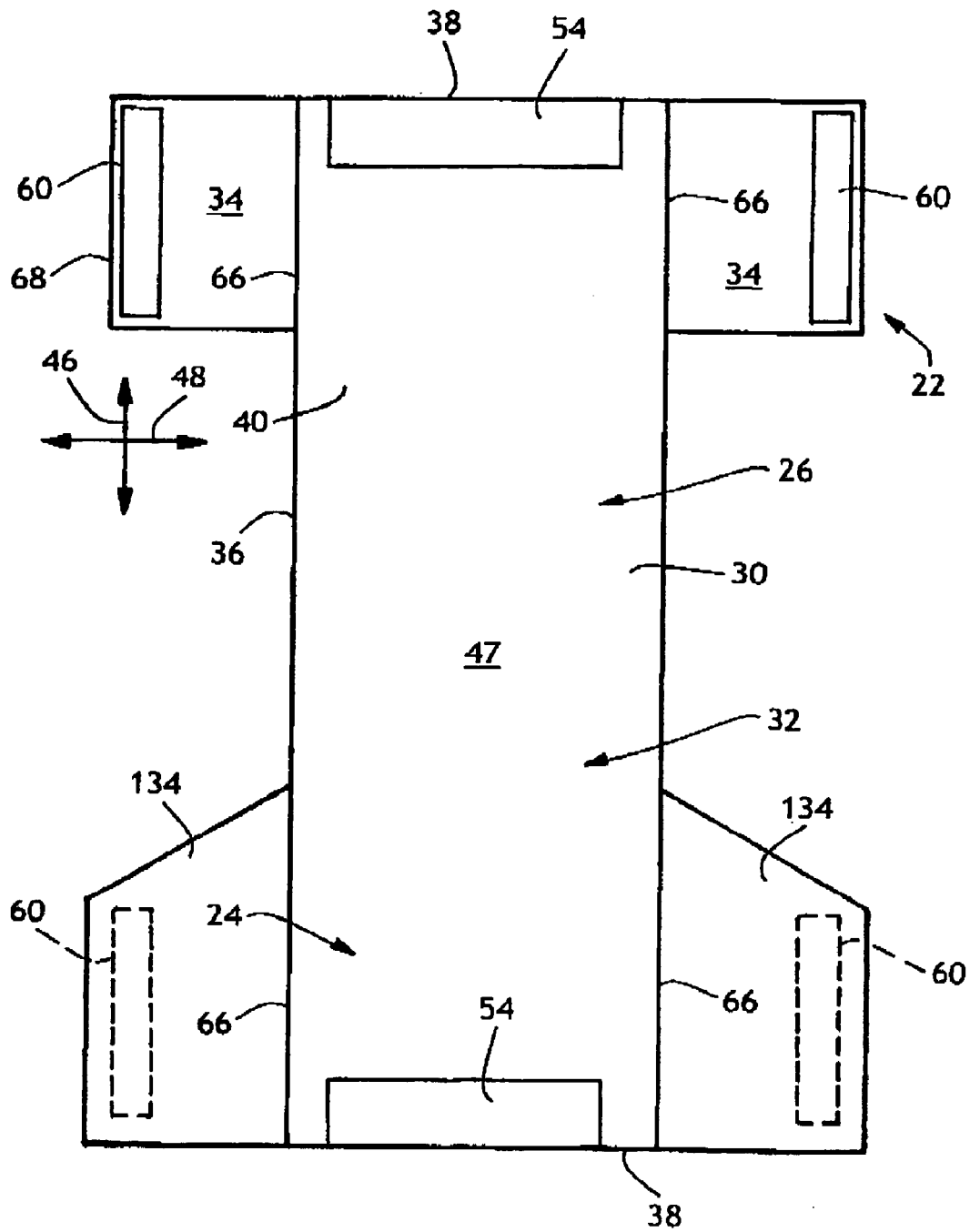
FIG. 2 representatively illustrates a plan view of the training pants of FIG. 1 in an unfastened, stretched and laid flat condition, and showing the surface of the training pants that faces away from the wearer.
Figure 3:
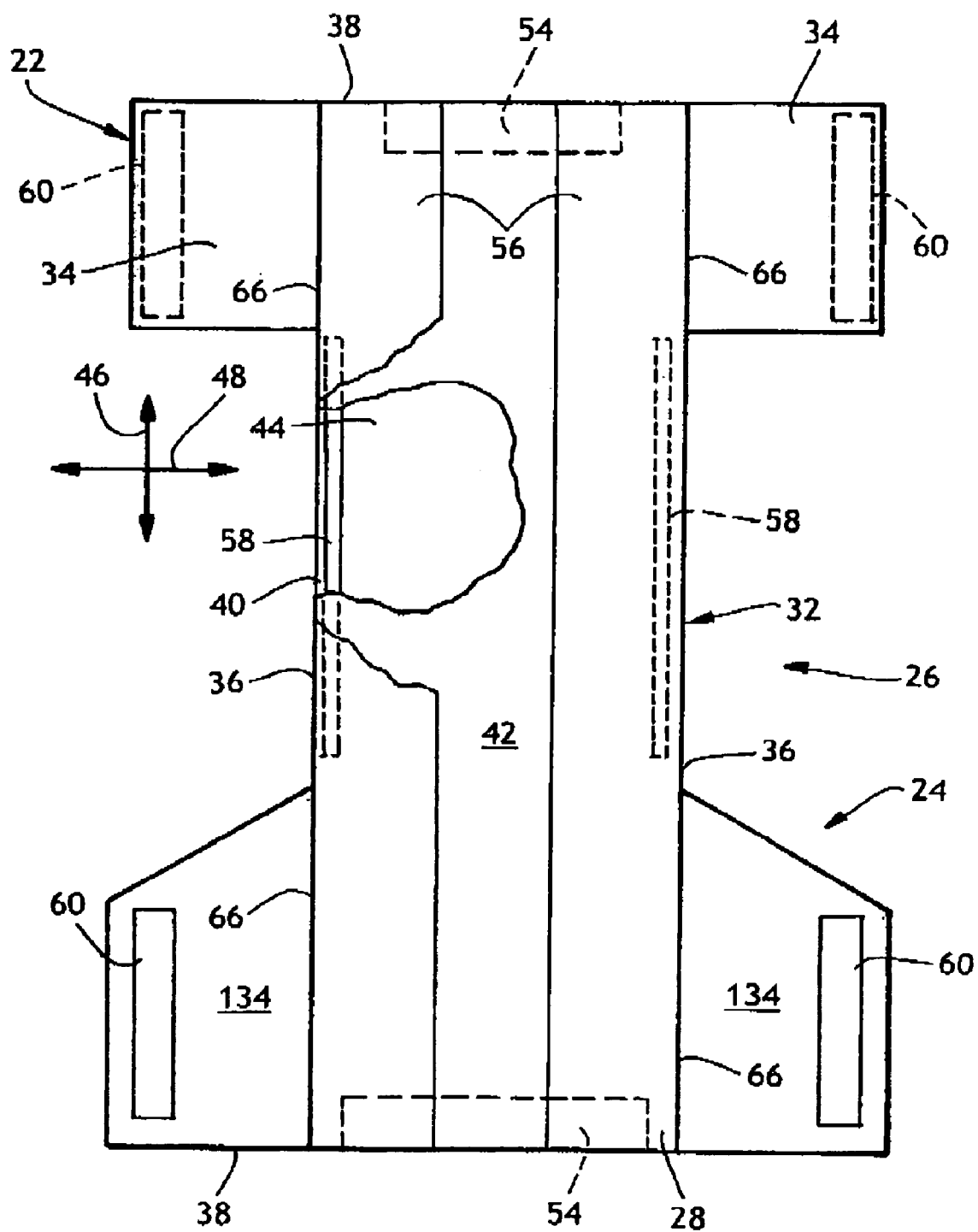
FIG. 3 representatively illustrates a plan view similar to FIG. 2, but showing the surface of the training pants that faces the wearer when worn, and with portions cut away to show underlying features.

The pair of training pants 20 is illustrated in FIG. 1 in a partially fastened condition. The pants 20 define a longitudinal direction 46 and a lateral direction 48 perpendicular to the longitudinal direction as shown in FIGS. 2 and 3. The pants 20 further define a pair of longitudinal end regions, otherwise referred to herein as a front waist region 22 and a back waist region 24, and a center region, otherwise referred to herein as a crotch region 26, extending longitudinally between and interconnecting the front and back waist regions 22, 24. The front and back waist regions 22, 24 includes those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The pants 20 also define an inner surface 28 adapted in use to be disposed toward the wearer, and an outer surface 30 opposite the inner surface. With additional reference to FIGS. 2 and 3, the pair of training pants 20 has a pair of laterally opposite side edges 36 and a pair of longitudinally opposite waist edges 38 (broadly, longitudinal ends).

The illustrated pants 20 can include an absorbent assembly, generally indicated at 32. For example, in the aspect of FIGS. 1-3, the training pants 20 include a generally rectangular central absorbent assembly 32 and side panels 34, 134 formed separately from and secured to the central absorbent assembly. The side panels 34, 134 can be bonded along seams 66 to the absorbent assembly 32 in the respective front and back waist regions 22, 24 of the pants 20. More particularly, the front side panels 34 can be permanently bonded to and extend laterally outward from the absorbent assembly 32 at the front waist region 22, and the back side panels 134 can be permanently bonded to and extend laterally from the absorbent assembly 32 at the back waist region 24. The side panels 34, 134 may be bonded to the absorbent assembly 32 using attachment means known to those skilled in the art such as adhesive, thermal or ultrasonic bonding.

The front and back side panels 34, 134, upon wearing of the pants 20, thus include the portions of the training pants 20 that are positioned on the hips of the wearer. The front and back side panels 34, 134 can be permanently bonded together to form the three-dimensional configuration of the pants 20, or be releasably connected with one another such as by a fastening system 60 of the illustrated aspects.

Suitable elastic materials, as well as one process of incorporating elastic side panels into training pants, are described in U.S. Pat. No. 4,940,464, issued on Jul. 10, 1990 to Van Gompel et al.; U.S. Pat. No. 5,224,405, issued on Jul. 6, 1993 to Pohjola; U.S. Pat. No. 5,104,116, issued on Apr. 14, 1992 to Pohjola; and U.S. Pat. No. 5,046,272, issued on Sep. 10, 1991 to Vogt et al.; all of which are incorporated herein by reference in their entirety to the extent they are consistent (i.e., not in conflict) herewith. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220, issued on May 5, 1987 to Wisneski et al.; U.S. Pat. No. 5,226,992, issued on Jul. 13, 1993 to Morman; European Patent Application No. EP 0 217 032, published on Apr. 8, 1987 in the name of Taylor et al.; and PCT application WO 01/88245 in the name of Welch et al.; all of which are incorporated herein by reference in their entirety to the extent they are consistent (i.e., not in conflict) herewith. As is known in the art, the side panels 34, 134 may include elastic material or stretchable but inelastic materials.

The absorbent assembly 32 is illustrated in FIGS. 1-3 as having a rectangular shape. However, it is contemplated that the absorbent assembly 32 may have other shapes (e.g., hourglass, T-shaped, I-shaped, and the like) without departing from the scope of this invention. It is also understood that the side panels 34, 134 may alternatively be formed integrally with the absorbent assembly 32 without departing from the scope of this invention. In such a configuration, the side panels 34, 134 and the absorbent assembly would include at least some common materials, such as the bodyside liner 42, outercover 40, other materials and/or combinations thereof.

The absorbent assembly 32 includes an outercover 40 and a bodyside liner 42 (FIG. 3) in a superposed relation therewith. The bodyside liner 42 can be suitably joined to the outercover 40 along at least a portion of the longitudinal ends of the pants 20. The bodyside liner 42 can be suitably adapted, i.e., positioned relative to the other components of the pants 20, to contact the wearer's skin during wear of the pants. The absorbent assembly 32 also includes an absorbent body 44 (FIG. 3) disposed between the outercover 40 and the bodyside liner 42 for absorbing liquid body exudates. The bodyside liner 42 can be suitably joined to the outercover 40 along at least a portion of the longitudinal ends of the pants 20. The bodyside-liner 42 and the outercover 40 can, for example, be attached to each other by adhesive, ultrasonic bonding, thermal bonding or by other suitable attachment techniques known in the art. Moreover, at least a portion of the absorbent body 44 can optionally be attached to the bodyside liner 42 and/or the outercover 40 utilizing the methods described above.

As mentioned above, the front and back side panels 34, 134 can be releasably connected with one another such as by the fastening system 60 of the illustrated aspect. With the training pants 20 in the fastened position as partially illustrated in FIG. 1, the front and back waist regions 22, 24 are connected together to define the three-dimensional pants configuration having a waist opening 50 and a pair of leg openings 52. The waist edges 38 (e.g., longitudinal ends) of the training pants 20 are configured to encircle the waist of the wearer to define the waist opening 50 (FIG. 1) of the pants.

The fastening system 60 may include any refastenable fasteners suitable for absorbent articles, such as adhesive fasteners, cohesive fasteners, mechanical fasteners, or the like. In one aspect of the invention, the fastening system includes mechanical fastening elements for improved performance. Suitable mechanical fastening elements can be provided by interlocking geometric-shaped materials, such as hooks, loops, bulbs, mushrooms, arrowheads, balls on stems, male and female mating components, buckles, snaps, or the like. For example, fastening systems are also disclosed in the previously-incorporated PCT Patent Application WO 00/37009, published on Jun. 29, 2000 by A. Fletcher et al. and the previously-incorporated U.S. Pat. No. 6,645,190, issued on Nov. 11, 2003 to Olson et al.

The pants 20 may further include a pair of containment flaps 56 for inhibiting the lateral flow of body exudates. As illustrated in FIG. 3, the containment flaps 56 can be operatively attached to the pants 20 in any suitable manner as is well known in the art. In particular, suitable constructions and arrangements for the containment flaps 56 are generally well known to those skilled in the art and are described in U.S. Pat. No. 4,704,116, issued on Nov. 3, 1987 to Enloe, which is incorporated herein by reference to the extent that it is consistent (i.e., not in conflict) herewith.

To further enhance containment and/or absorption of body exudates, the training pants 20 may include waist elastic members 54 in the front and/or back waist regions 22, 24 of the pants 20. Likewise, the pants 20 may include leg elastic members 58, as are known to those skilled in the art. The waist elastic members 54 and the leg elastic members 58 can be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament spandex elastomeric threads sold under the trade name LYCRA and available from Invista of Wilmington, Del., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent body 44. A suitable liquid permeable bodyside liner 42 is a nonwoven polyethylene/polypropylene bicomponent web having a basis weight of about 27 gsm; the web may be spunbonded or a bonded carded web. Optionally, the bodyside liner 42 may be treated with a surfactant to increase the wettability of the liner material.

Alternatively, the bodyside liner 42 may also be stretchable, and in some aspects it may be elastomeric. For instance, the bodyside liner 42 can be a non-woven, spunbond polypropylene fabric composed of about 2 to 3 denier fibers formed into a web having a basis weight of about 12 gsm which is necked approximately 60 percent. Strands of about 9 gsm KRATON G2760 elastomer material placed eight strands per inch (2.54 cm) can be adhered to the necked spunbond material to impart elasticity to the spunbond fabric. The fabric can be surface treated with an operative amount of surfactant, such as about 0.6 percent AHCOVEL Base N62 surfactant, available from ICI Americas, a business having offices in Wilmington, Del., U.S.A. Other suitable materials may be extensible biaxially stretchable materials, such as a neck stretched/creped spunbond. Reference is made to U.S. Pat. No. 6,552,245, issued on Apr. 22, 2003 to Roessler et al., which is incorporated herein by reference to the extent that it is consistent (i.e., not in conflict) herewith.

An absorbent body 44 may be disposed on the outercover 40, for example, between the outercover 40 and the bodyside liner 42. The outercover 40 and the bodyside liner 42 can be joined together by any suitable means such as adhesives, ultrasonic bonds, thermal bonds, or the like. The absorbent body 44 can be in a variety of shapes and configurations as are known in the art, such as rectangular, hourglass shaped, I-shaped, and the like. Further, at least a portion of the absorbent body 44 can optionally be attached to the bodyside liner 42 and/or the outercover 40 utilizing the methods described above.

The absorbent body 44 is suitably compressible, conformable, and capable of absorbing and retaining liquid body exudates released by the wearer. For example, the absorbent assembly can include a matrix of absorbent fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The absorbent body 44 can have a density within the range of about 0.10 to about 0.5 grams per cubic centimeter and may be wrapped or encompassed by a suitable tissue or nonwoven wrap for maintaining the integrity and/or the shape of the absorbent assembly.

In one aspect, the absorbent body 44 may be stretchable so as not to inhibit the stretchability of other components to which the absorbent body may be adhered, such as the outercover 40 and/or the bodyside liner 42. For example, the absorbent body may include materials disclosed in U.S. Pat. No. 5,964,743, issued on Oct. 12, 1999 to Abuto et al.; U.S. Pat. No. 5,645,542, issued on Jul. 8, 1997 to Anjur et al.; U.S. Pat. No. 6,231,557, issued on May 15, 2001 to Krautkramer et al.; U.S. Pat. No. 6,362,389, issued on Mar. 26, 2002 to McDowall et al.; and international patent application WO 03/051254, the disclosure of each of which is incorporated herein by reference to the extent that it is consistent (i.e., not in conflict) herewith.

In some aspects, a surge management layer (not shown) may be included in the pants 20. The surge management layer may be positioned in the pants 20 in a variety of locations as is known in the art. For example, the surge management layer can be proximate the absorbent body 44, for example between the absorbent body 44 and the bodyside liner 22, and attached to one or more components of the pants 20 by methods known in the art, such as by adhesive, ultrasonic, or thermal bonding.

A surge management layer helps to decelerate and diffuse surges or gushes of liquid that may be rapidly introduced into the absorbent body 44. Desirably, the surge management layer can rapidly accept and temporarily hold the liquid prior to releasing the liquid into the storage or retention portions of the absorbent body 44. Examples of suitable surge management layers are described in U.S. Pat. No. 5,486,166, issued on Jan. 23, 1996 to Bishop et al. and U.S. Pat. No. 5,490,846, issued on Feb. 13, 1996 to Ellis et al., the contents of which are incorporated herein by reference to the extent that they are consistent (i.e., not in conflict) herewith.

The outercover 40 may suitably include a material that is substantially liquid impermeable. The outercover 40 may suitably include a multi-layered laminate structure in which at least one of the layers is liquid impermeable. In particular aspects, the outer layer may suitably provide a relatively cloth-like texture to the wearer. A suitable liquid impermeable film for use as a liquid impermeable inner layer, or a single layer liquid impermeable outercover 40 is a 0.025 millimeter (1.0 mil) polyethylene film commercially available from Edison Plastics Company of South Plainfield, N.J. Alternatively, the outercover 40 may include a woven or non-woven fibrous web layer that has been totally or partially constructed or treated to impart the desired levels of liquid impermeability to selected regions that are adjacent or proximate the absorbent body.

The outercover 40 may also be stretchable, and in some aspects it may be elastomeric. For example, such an outercover material can include a 0.3 ounces per square inch (osy) polypropylene spunbond that is necked 60 percent in the lateral direction 46 and creped 60 percent in the longitudinal direction 48, laminated with 3 grams per square meter (gsm) Bostik-Findley H2525A styrene-isoprene-styrene based adhesive to 8 gsm PEBAX 2533 film with 20 percent $TiO_2$ concentrate. Reference is made to U.S. Pat. No. 5,883,028, issued on Mar. 16, 1999 to Morman et al.; U.S. Pat. No. 5,116,662, issued on May 26, 1992 to Morman; and U.S. Pat. No. 5,114,781, issued on May 19, 1992 to Morman; all of which are incorporated herein by reference to the extent that they are consistent (i.e., not in conflict) herewith, for additional information regarding suitable outercover materials.

The outercover 40 may also be a laminate including at least two coupled layers. For examples and for additional information regarding suitable outercover materials, reference is made to U.S. Pat. No. 6,156,421, issued on Dec. 5, 2000 to Stopper et al.; U.S. Pat. No. 6,096,014, issued on Aug. 1, 2000 to Haffner et al.; U.S. Pat. No. 5,843,057, issued on Dec. 1, 1998 to McCormack; and U.S. Pat. No. 4,725,473, issued on Feb. 16, 1988 to Van Gompel et al.; all of which are incorporated herein by reference to the extent that they are consistent (i.e., not in conflict) herewith.

Registration of a graphic-carrying material is described in more detail in the previously-incorporated U.S. Pat. No. 5,766,389, issued on Jun. 16, 1998 to Brandon et al.; U.S. Pat. No. 5,612,118, issued on Mar. 18, 1997 to Schleinz et al.; and U.S. Pat. No. 6,231,715, issued on May 15, 2001 to Schleinz et al.; which are incorporated herein by reference to the extent that they are consistent (i.e., not in conflict) herewith. The first of these references describes a distinctive process and apparatus for registering a plurality of distinct and separate components on a continuously moving first layer of material with a respective plurality of distinct and separate components on a continuously moving second layer of material. The second layer of material has the components suitably represented by respective reference marks, both provided thereon at a uniform repeat length shorter than a machine product repeat length. The distance between two successive reference marks is determined and then used to calculate a desired speed for the current process conditions. The second layer of material is then controllably stretched or relaxed so that the distance between two successive reference marks substantially equals the selected distance, which in this case is one machine product repeat length; this is termed the repeat loop. The second layer is then controllably registered to the first layer of material so that each reference mark is selectively registered with a respective component; this is termed the placement loop. The amount of stretch or relaxation can be controllably adjusted by varying the speed and/or tension of the second layer. The term reference mark can refer, but is not limited, to structure such as waist or leg elastics, adhesive beads, corners or edges of structure, transporting mediums such as conveyor belts, visual marks, magnetic marks, electrical marks, electromagnetic marks, optical brighteners sensitive to ultraviolet radiation, or the like, all of which can be sensed, detected, or otherwise identified by an appropriate device. The term machine product repeat length refers to a selected distance, which in this example is the measured distance between successive, like components during manufacture (e.g., between successive waist bands, absorbent pads, or the like). In other words, the machine product repeat length is the length of one product during the manufacturing process. Thus, when a reference mark is registered with a component of the first layer, then the component represented by that reference mark is registered with the component of the first layer.

One or more of the outercover 40, the front and back waist regions 22, 24, the containment flaps 56, and the surge management layer may suitably include a liquid-permeable or liquid-impermeable laminated material that is selected to exhibit a low Poisson's Ratio to facilitate the conversion process. The Poisson's Ratio of a material is an indication of the necking experienced by a material, where necking is a reduction in transverse or cross-machine direction 46 when the material is stressed in the longitudinal or machine direction 48. More specifically, Poisson's ratio is the ratio of transverse contraction strain to longitudinal extension strain in the direction of stretching force:

$$\text{Poisson's Ratio} = -\epsilon_{transverse}/\epsilon_{longitudinal}$$

where strain is defined in elementary form as the change in length divided by the original length.

Figure 4:
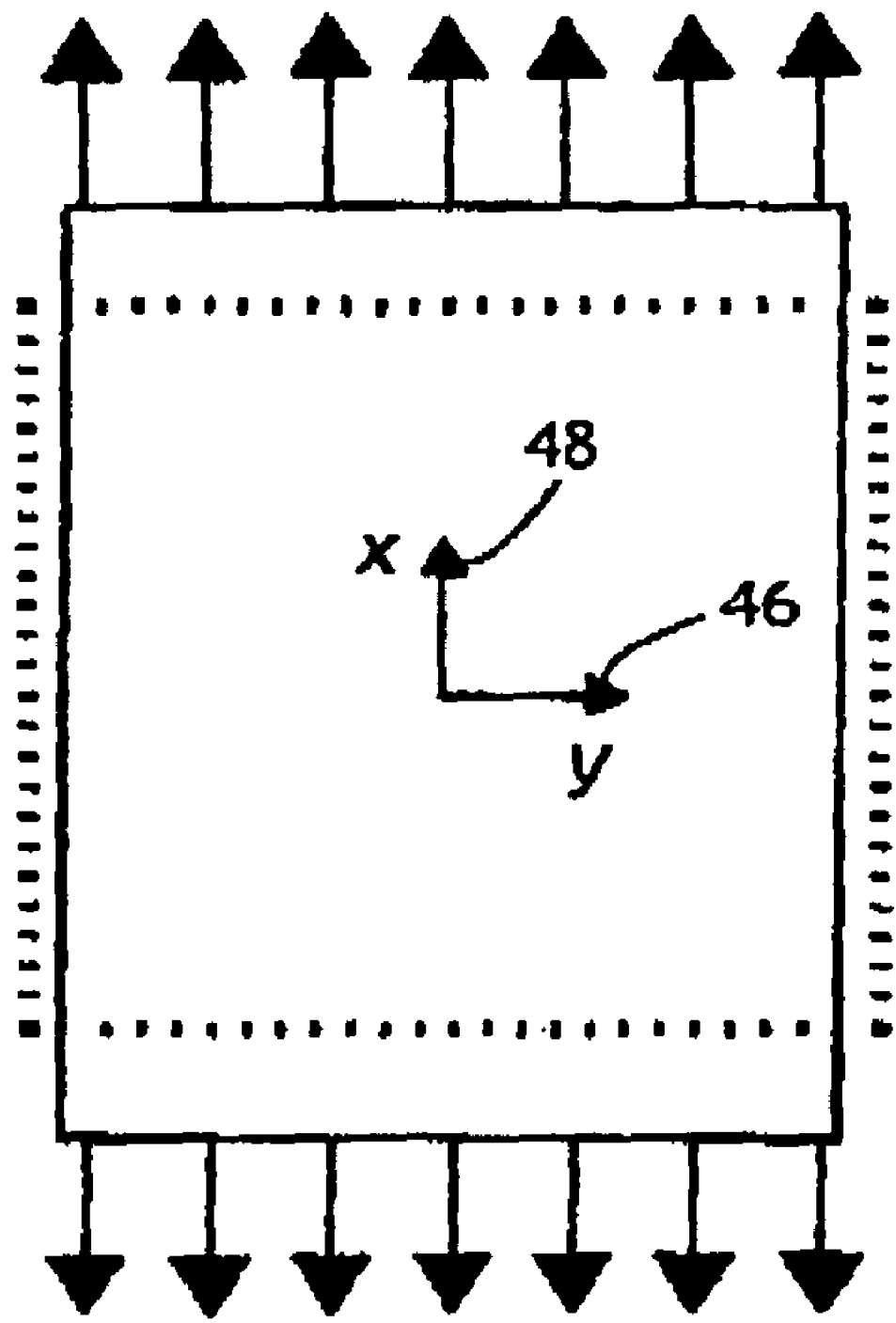
FIG. 4 schematically illustrates the forces associated with a Poisson's Ratio test.

The Poisson's Ratio of a material may be determined by using a variety of test methods, including ASTM-E132, as illustrated in FIG. 4. In this test method, Poisson's Ratio is the negative ratio of lateral strain (in the y-direction 46) to axial strain (in the x-direction 48) or Poisson's Ratio=$-\epsilon_y/\epsilon_x$. Testing is performed by running a tensile test on a specimen equipped with two extensometers. One extensometer is aligned parallel to the applied tensile stress, where tensile stress is applied in the x-direction 48, while the second extensometer is aligned perpendicular to the tensile stress.

The laminated material may be suitably selected such that it exhibits a Poisson's Ratio less than 1.0 and 2.0 at longitudinal strains of 4 percent and 6 percent, respectively. The laminated material optimally exhibits a Poisson's Ratio less than 0.75 and 1.5 at longitudinal strains of 4 percent and 6 percent, respectively. The laminated material more optimally exhibits a Poisson's Ratio less than 0.4 and 0.5 at longitudinal strains of 4 percent and 6 percent, respectively.

In one aspect of the present invention, a suitable laminated material exhibiting low Poisson's Ratios is an adhesive spunbond film laminate (aSFL). Preparation of such material is essentially similar to that used to prepare laminates as described herein. A low Poisson's ratio for a laminate is achieved by having disparate tensions between the spunbond nonwoven and film layers of the laminate. Because a spunbond nonwoven alone typically exhibits a higher Poisson's Ratio than a film alone, the spunbond nonwoven in this process is maintained at a slightly lower tension than that of the film at the point of lamination, yielding a laminate that exhibits a low Poisson's Ratio. The tension may be adjusted until the desired Poisson's Ratio is achieved, including increasing the tension of the film to its maximum setpoint, and decreasing the tension of the spunbond nonwoven to its minimum setpoint. To obtain a laminate with a higher Poisson's Ratio, the opposite actions are taken such that the film is maintained at a slightly lower tension than that of the spunbond nonwoven at the point of lamination.

An example illustrates the potential improvements available through the use of a laminated material exhibiting a low Poisson's Ratio. A standard laminate was used to make outercovers 40 in the manufacture of pants 20. This laminate exhibited variable and unacceptable registration and/or product quality. The standard laminate was tested using ASTM-E132 and exhibited a Poisson's Ratio of 1.6 at 4 percent longitudinal strain and of 2.4 at 6 percent longitudinal strain. Under the processes described herein, nine rolls of aSFL material were produced using a 0.6 osy spunbond polypropylene nonwoven, a 0.5 osy film, and 1.5 grams per square meter REXTAC 2215 brand adhesive. Process conditions included setting the spunbound and nonwoven at decreasing tensions to include minimum tension settings and setting the film at increasing tensions to include maximum tension. Material data for these rolls using ASTM-E132 is listed in Table 1.

TABLE 1

| | Poisson's Ratio at % Longitudinal Strain | | | | | | |
|---|---|---|---|---|---|---|---|
| Roll # | 1% | 3% | 4% | 5% | 6% | 7% | 9% |
| 1 | 0.98 | 0.76 | 1.03 | 1.30 | 1.56 | 1.81 | 1.99 |
| 2 | 0.98 | 1.09 | 1.26 | 1.44 | 1.70 | 1.96 | 2.18 |
| 3 | 0.65 | 0.98 | 1.24 | 1.50 | 1.68 | 1.87 | 2.11 |
| 4 | 0.65 | 0.65 | 0.91 | 1.17 | 1.38 | 1.58 | 1.77 |
| 5 | 0.33 | 0.49 | 0.78 | 1.08 | 1.31 | 1.54 | 1.91 |

TABLE 1-continued

| | Poisson's Ratio at % Longitudinal Strain | | | | | | |
|---|---|---|---|---|---|---|---|
| Roll # | 1% | 3% | 4% | 5% | 6% | 7% | 9% |
| 6 | 0.49 | 0.71 | 1.04 | 1.37 | 1.57 | 1.77 | 2.02 |
| 7 | 0.16 | 0.65 | 0.88 | 1.30 | 1.56 | 1.83 | 2.02 |
| 8 | 0.33 | 0.49 | 0.74 | 0.98 | 1.24 | 1.49 | 1.78 |
| 9 | 0.65 | 0.54 | 0.86 | 1.17 | 1.42 | 1.67 | 1.95 |

These samples of aSFL laminated material were then printed and converted to make outercovers 40 in the manufacture of pants 20. These aSFL laminated materials demonstrated consistent and acceptable registration and product quality results.

As various changes could be made in the above constructions and methods, without departing from the scope of the invention, it is intended that all matter contained in the above description and shown in the accompanying drawings shall be interpreted as illustrative and not in a limiting sense.

When introducing elements of the invention or the preferred aspect(s) thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. An absorbent article defining a longitudinal direction and a lateral direction perpendicular to the longitudinal direction, the absorbent article comprising:
   an outercover, the outercover comprising a laminated material including first and second-layers, the second layer having been joined to the first layer at a point of lamination while the second layer was maintained at a lower tension than the first layer at the point of lamination;
   an absorbent body disposed adjacent the outercover; and
   a graphic associated with the outercover, wherein the laminated material exhibits a Poisson's Ratio less than 1.0 at 4 percent longitudinal strain using ASTM-E132.

2. The absorbent article of claim 1, wherein the laminated material exhibits a Poisson's Ratio less than 0.75 at 4 percent longitudinal strain using ASTM-E132.

3. The absorbent article of claim 1, wherein the laminated material exhibits a Poisson's Ratio less than 0.4 at 4 percent longitudinal strain using ASTM-E132.

4. The absorbent article of claim 1, wherein a first layer is a film.

5. The absorbent article of claim 1, wherein a second layer is a spunbond nonwoven.

6. The absorbent article of claim 5, wherein the second layer is an outermost layer.

7. The absorbent article of claim 1, wherein the graphic is registered with respect to the article.

8. The absorbent article of claim 1, wherein the graphic is printed on the outercover.

9. The absorbent article of claim 1, wherein the outercover is liquid impermeable.

10. An absorbent article defining a longitudinal direction and a lateral direction perpendicular to the longitudinal direction, the absorbent article comprising:
    an outercover, the outercover comprising a laminated material including first and second-layers, the second layer having been joined to the first layer at a point of lamination while the second layer was maintained at a lower tension than the first layer at the point of lamination;
    an absorbent body disposed adjacent the outercover; and
    a graphic associated with the outercover, wherein the laminated material exhibits a Poisson's Ratio less than 2.0 at 6 percent longitudinal strain using ASTM-E132.

11. The absorbent article of claim 10, wherein the laminated material exhibits a Poisson's Ratio less than 1.5 at 6 percent longitudinal strain using ASTM-E132.

12. The absorbent article of claim 10, wherein the laminated material exhibits a Poisson's Ratio less than 0.5 at 6 percent longitudinal strain using ASTM-E132.

13. The absorbent article of claim 10, wherein the outercover is liquid impermeable.

14. An absorbent article defining a longitudinal direction and a lateral direction perpendicular to the longitudinal direction, the absorbent article comprising:
    a laminated material including first and second layers, the second layer having been joined to the first layer at a point of lamination while the second layer was maintained at a lower tension than the first layer at the point of lamination;
    a graphic associated with the laminated material; and
    an absorbent body disposed in the absorbent article, wherein the graphic is registered to the absorbent body, and wherein the laminated material exhibits a Poisson's Ratio less than 1.0 at 4 percent longitudinal strain using ASTM-E132.

15. The absorbent article of claim 14, further comprising an outercover, wherein the outercover includes the laminated material.

16. The absorbent article of claim 14, wherein the graphic is printed on the laminated material.

17. A laminated material for use in a product, the laminated material comprising
    a film layer including a film; and
    a nonwoven layer including a spunbond nonwoven, the nonwoven layer having been joined to the film layer at a point of lamination while the nonwoven layer was maintained at a lower tension than the film layer at the point of lamination, wherein the laminated material exhibits a Poisson's Ratio less than 1.0 at 4 percent longitudinal strain using ASTM-E132.

18. The laminated material of claim 17, wherein the laminated material exhibits a Poisson's Ratio less than 0.75 at 4 percent longitudinal strain using ASTM-E132.

19. The laminated material of claim 17, wherein the laminated material, exhibits a Poisson's Ratio less than 0.4 at 4 percent longitudinal strain using ASTM-E132.

20. The laminated material of claim 17, further comprising an adhesive coupling the film layer to the nonwoven layer.

21. The laminated material of claim 17, wherein the product is an absorbent article.

* * * * *